(12) United States Patent
Takehisa et al.

(10) Patent No.: US 10,156,664 B2
(45) Date of Patent: Dec. 18, 2018

(54) MASK INSPECTION APPARATUS AND MASK INSPECTION METHOD

(71) Applicant: Lasertec Corporation, Yokohama (JP)

(72) Inventors: Kiwamu Takehisa, Yokohama (JP); Hiroki Miyai, Yokohama (JP)

(73) Assignee: Lasertec Corporation, Yokohama (JP)

(*) Notice: Subject to any disclaimer, the term of this patent is extended or adjusted under 35 U.S.C. 154(b) by 32 days.

(21) Appl. No.: 15/331,575

(22) Filed: Oct. 21, 2016

(65) Prior Publication Data
US 2017/0235031 A1  Aug. 17, 2017

(30) Foreign Application Priority Data

Feb. 12, 2016 (JP) ................. 2016-024904
Feb. 12, 2016 (JP) ................. 2016-024905

(51) Int. Cl.
*G01N 21/88* (2006.01)
*G02B 5/08* (2006.01)
(Continued)

(52) U.S. Cl.
CPC .......... *G02B 5/0891* (2013.01); *B08B 7/0042* (2013.01); *B08B 7/0057* (2013.01);
(Continued)

(58) Field of Classification Search
CPC ................. G01N 21/95; G01N 21/956; G01N 21/95623; G01N 21/94; G01N 21/88
(Continued)

(56) References Cited

U.S. PATENT DOCUMENTS 5,838,433 A * 11/1998 Hagiwara ........ G01N 21/95623
356/339
6,954,266 B2 * 10/2005 Tomie .............. G01N 21/95623
250/492.2
(Continued)

FOREIGN PATENT DOCUMENTS

JP         H0682729 B2     10/1994
JP         2005536899 A    12/2005
(Continued)

OTHER PUBLICATIONS

Yamane, T. et al., "Actinic EUVL mask blank inspection and phase defect characterization," Proceedings of SPIE 7379, Photomask and Next-Generation Lithography Mask Technology XVI, 73790H, Apr. 8, 2009, Yokohama, Japan, 7 pages.
(Continued)

*Primary Examiner* — Audrey Y Chang
(74) *Attorney, Agent, or Firm* — McCoy Russell LLP

(57) ABSTRACT

Provided are a mask inspection apparatus and a mask inspection method that can prevent a reduction in a reflectance of a drop-in mirror, which is caused by carbon contaminants. A mask inspection apparatus according to the present invention includes a drop-in mirror including multi-layer film and a reflective surface. The drop-in mirror is configured to reflect illumination light incident on the reflective surface and illuminate the mask. An area of the reflective surface is configured to be greater than an area of an illuminated spot irradiated with the illumination light on the reflective surface. The drop-in mirror is configured to be movable. A position of the illuminated spot on the reflective surface is configured to be moved when the drop-in mirror is moved.

4 Claims, 17 Drawing Sheets

(51) Int. Cl.

| | | |
|---|---|---|
| *G02B 5/18* | (2006.01) | |
| *G02B 7/182* | (2006.01) | |
| *G02B 19/00* | (2006.01) | |
| *G02B 17/00* | (2006.01) | |
| *B08B 7/00* | (2006.01) | |
| *G01N 21/00* | (2006.01) | |
| *G01N 21/958* | (2006.01) | |

(52) U.S. Cl.
CPC ............ *G01N 21/00* (2013.01); *G01N 21/88* (2013.01); *G01N 21/958* (2013.01); *G02B 5/0816* (2013.01); *G02B 5/1814* (2013.01); *G02B 5/1838* (2013.01); *G02B 7/1821* (2013.01); *G02B 17/004* (2013.01); *G02B 19/0095* (2013.01)

(58) Field of Classification Search
USPC .............. 356/237.1, 339; 355/53, 63, 67, 77
See application file for complete search history.

(56) References Cited

U.S. PATENT DOCUMENTS

| | | | | |
|---|---|---|---|---|
| 7,746,461 B2* | 6/2010 | Aizawa | ................. | G01N 21/94 |
| | | | | 356/237.1 |
| 2012/0002184 A1* | 1/2012 | Bader | ................. | G03F 7/70108 |
| | | | | 355/67 |

FOREIGN PATENT DOCUMENTS

| | | |
|---|---|---|
| JP | 2006284595 A | 10/2006 |
| JP | 20100186995 | 8/2010 |
| JP | 5008012 B2 | 8/2012 |
| JP | 2013080810 A | 5/2013 |

OTHER PUBLICATIONS

Anazawa, T. et al., "Novel Ozone-based Cleaning Technique for EUV Masks and Optics Carbon Contamination," 2009 International Symposium on Extreme Ultraviolet Lithography (EUVL 09), vol. 1, Oct. 18, 2009, Prague, Czech Republic, 10 pages.

Shibata, R. et al., "Development of low-pressure UV cleaning technique for carbon contaminated EUV optics," 2010 International Symposium on Extreme Ultraviolet Lithography (EUVL 10), Oct. 18, 2010, Kobe, Japan, 18 pages.

Kriese, M. et al., "Development of EUVL Collector Technologies for Infrared Radiation Suppression," 2013 International Symposium on Extreme Ultraviolet Lithography (EUVL 13), Oct. 6, 2013, Toyama, Japan, 30 pages.

Ichimaru, S. et al., "Mo/Si multilayer mirrors with 300-bilayers for EUV lithography," Proceedings of SPIE 9658, Photomask Japan 2015: Photomask and Next-Generation Lithography Mask Technology XXII, 965814, Apr. 20, 2015, Yokahama, Japan, 5 pages.

Japan Patent Office, Office Action Issued in Japan Patent Application No. 2016-024904, Jul. 5, 2016, 10 pages. Submitted with Partial Translation).

Japan Patent Office, Office Action Issued in Japan Patent Application No. 2016-024905, Jul. 5, 2016, 7 pages. (Submitted with Partial Translation).

* cited by examiner

MASK INSPECTION APPARATUS AND MASK INSPECTION METHOD

CROSS REFERENCE TO RELATED APPLICATIONS

The present application claims priority to Japanese Patent Application No. 2016-024904, filed on Feb. 12, 2016, and Japanese Patent Application No. 2016-024905, filed on Feb. 12, 2016. The entire contents of the above-referenced applications are hereby incorporated by reference in their entirety for all purposes.

BACKGROUND OF THE INVENTION

1. Field of the Invention

The present invention relates to a mask inspection apparatus for EUVL (Extremely Ultraviolet Lithography), and in particular, to a mask inspection apparatus and a mask inspection method called an Actinic inspection that uses EUV light with a wavelength of 13.5 nm, which is the same as an exposure wavelength, as illumination light.

2. Description of Related Art

In the lithography technology for miniaturizing semiconductors, currently the ArF lithography that uses an ArF excimer laser with an exposure wavelength of 193 nm as an exposure light source is employed for mass production. A liquid immersion technique in which a gap between an objective lens of an exposure apparatus and a wafer is filled with water in order to improve the resolution, which is called ArF immersion lithography, is becoming widely used for mass production. Development of technology for promoting practical use of EUVL with an exposure wavelength of 13.5 nm in order to further improve miniaturization of the semiconductors has become widespread.

A mask used for EUVL (hereinafter referred to as an EUV mask) has a layered structure in which a multi-layer film for reflecting extreme ultraviolet (extreme ultraviolet used in EUVL will be hereinafter referred to as EUV light) is formed on a substrate made of a low thermal expansion glass. The multi-layer film has a structure in which molybdenum (Mo) and Silicon (Si) are alternately layered in several tens of layers (often referred as a Mo/Si multi-layer film). The multi-layer film can reflect about 65% of EUV light with a wavelength of 13.5 nm, which is vertically incident on the multi-layer.

An absorber that absorbs the EUV light (e.g., tantalum boron nitride (TaBN)) is deposited on the multi-layer film, and then a blank (a mask without a pattern) is formed. Note that a protective film is formed between the absorber and the multi-layer film. After the blank is formed, a resist process is used to form the absorber in a pattern. Thus, a patterned EUV mask is completed.

A blanks inspection apparatus that inspects defects in a blank using an EUV light source is called an ABI (Actinic M blank inspection) apparatus. A basic configuration of an optical system of an ABI apparatus 900 according to related art is shown in FIG. 10.

As shown in FIG. 10, illumination light EUV901 including EUV light with a wavelength of 13.5 nm is emitted from an EUV light source 901 toward a mask M901, which is to be inspected, reflected by large ellipsoidal mirrors 902a and 902b, and then travels while being narrowed like illumination light EUV902. Then, the light is reflected by a drop-in mirror 903a to travel toward the mask M901 side, so that illumination light EUV903 is incident almost vertically on a small area on a surface of a mask blank of the mask M901. Although specularly reflected light reflected by the mask M901 travels in a direction opposite to a direction in which the illumination light EUV903 travels, if there is a defect in the small area, scattered light S901 is generated.

The scattered light S901 travels while spreading at an angle greater than that of the specularly reflected light. Then, the scattered light S901 travels upward around the drop-in mirror 903a, is incident on a concave mirror 905 that constitutes a Schwarzschild optical system 904. The scattered light S901 reflected by the concave mirror 905 is incident on a convex mirror 906 and then reflected by the convex mirror 906. Scattered light S902 reflected by the convex mirror 906 travels upward and is incident on a CCD detector 907.

The Schwarzschild optical system 904 is designed to magnify a small area on the mask blank of the mask M901 that is illuminated by the illumination light EUV903 by about 26 times and project the small area on the CCD detector 907. This enables an observation of a defect present on a surface of the mask blank of the mask M901. The ABI apparatus 900 is described by, for example, Takashi Yamane, et al, "Actinic EUVL M blank inspection and phase defect characterization," Proceedings of SPIE, Vol. 7379, 73790H (2009).

As described above, in the ABI apparatus 900, light generated from the surface of the mask M901 reaches the CCD detector 907 only when a defect is present. Accordingly, when there is no defect, no signal is output from the CCD detector 907. When there is no defect, an image will be dark. The inspection shown in FIG. 10 is referred to as a dark field inspection.

On the other hand, as shown in FIG. 11, when a defect is detected on the mask M901, an inspection is performed in such a way that specularly reflected light 910b of the illumination light EUV903 that illuminates the small area including a defect is made to be incident on the CCD detector 907 in order to enable a shape and a size of the defect to be examined. Such an inspection is referred to as a bright field inspection. That is, when the illumination light EUV903 is incident on the surface of the mask M901, a drop-in mirror 903b for bright field illumination is adjusted in order for the illumination light EUV903 to illuminate the small area at an oblique angle of incidence of about 6 degrees. Consequently, specularly reflected light 910b is generated.

The specularly reflected light 910b is incident on the Schwarzschild optical system 904 to finally reach the CCD detector 907, thereby enabling an observation of a shape of the defect. However, as defects are small, the shapes thereof cannot be accurately recognized by the magnification of about 26 times, which is made by the Schwarzschild optical system 904. Thus, the small area is further magnified by several tens of times by a planar mirror 908 and a concave mirror 909, and the small area is highly magnified by about several hundreds of times to 1200 times in total. This enables an accurate observation of the shape of the defect. Note that in the ABI apparatus 900, such a function for switching to a magnifying optical system for EUV capable of a high magnification is disclosed in, for example, Japanese Patent No. 5008012.

In most cases, EUV light is absorbed in the atmosphere, and an intensity of the EUV light is reduced. For this reason, exposures and inspections using the EUV light are performed in a vacuum. There is a problem that if the power of the EUV light is large, stains such as carbon compounds (carbon contaminants) or the like are attached to a reflective surface of a mirror that reflects the EUV light, thereby reducing the reflectance. For example, the following cleaning method for removing the stains such as carbon contaminants adhered to the mirror is suggested.

In a method for outputting VUV (Vacuum UV) light from a VUV lamp in an oxygen or ozone atmosphere, firstly, the oxygen or ozone is excited by VUV light, and then atomic oxygen (oxygen radicals) is generated. The generated oxygen radicals decompose stains such as carbon contaminants or the like. Note that the cleaning method for carbon contaminants is disclosed by, for example, Toshihisa Anazawa, et al, "Novel Ozone-based Cleaning Technique for EUV Ms and Optics Carbon Contamination," International Symposium on Extreme Ultraviolet Lithography (2009) and by Ryo Shibata, et al, "Development of low-pressure UV cleaning technique for carbon contaminated EUV optics," International Symposium on Extreme Ultraviolet Lithography (2010) etc.

In another method, hydrogen gas is made to flow inside an apparatus, and then hydrogen radicals are generated by EUV light in the exposure light or inspection light. The generated hydrogen radicals decompose stains such as carbon contaminants or the like. An amount of absorption of EUV light by hydrogen is smaller than that by other kinds of gas such as oxygen and the like. Therefore, an advantage of using hydrogen radicals is that mirrors can be cleaned while performing exposure.

One of problems in the ABI apparatus 900 according to the related art will be described based on the ABI apparatus 900 shown in FIGS. 10 and 11. The problem is that stains are easily deposited on reflective surfaces of the drop-in mirrors 903a and 903b. The stains contain, for example, carbon compounds. The stains containing carbon compounds are referred to as carbon contaminants. These stains reduce the reflectance of EUV light and reduce the power of reflected light. It is considered that one of the causes for this is that small quantities of the carbon compounds present inside the ABI apparatus 900, which is under vacuum, are decomposed by the irradiation of the EUV light and then adhered to the reflective surfaces. In particular, the greater the intensity of the EUV light that is incident on the reflective surfaces, the greater the speed at which stains such as carbon contaminants or the like are generated will become.

For example, in the ABI apparatus 900 shown in FIG. 10, a size of a spot (an illuminated spot) of the illumination light EUV 902 that is incident on the drop-in mirror 903a is smaller than those on the ellipsoidal mirrors 902a and 902b by two orders of magnitude by an area ratio. Therefore, an intensity of the illumination light on the illuminated spot will become extremely high. Thus, the generation speed of stains such as carbon contaminants or the like is increased. As described above, there has been a problem in the mask inspection apparatus that stains such as carbon contaminants or the like are generated on the drop-in mirror 903a in a short time.

As shown in FIG. 11, a magnifying optical system with a high magnification is employed in a bright field inspection that is carried out in order to observe a small defect. However, as the intensity of the light reaching the CCD detector 907 is reduced in inverse proportion to a square of the magnification, it is necessary to increase the intensity of illumination light by an order(s) of magnitude so that light with a sufficient intensity will be incident on the CCD detector 907.

It is obvious that although an observation with a high magnification can be carried out with a low intensity of the illumination light, it is necessary to increase the exposure time by the CCD detector 907 to be extremely long. Therefore, inspections are more susceptible to the influence of an environment such as one with vibrations and the like during the long exposure time. It is thus necessary to increase the power of the illumination light in order to observe a defect in a short time. However, when the power of the illumination light is increased, there has been a problem that stains such as carbon contaminants or the like are generated in a shorter time, and thus the reflective surfaces need to be frequently cleaned.

Further, the mirror cleaning method for EUV exposure apparatuses according to the related art is characterized in that mirrors can be cleaned while performing exposure. However, in this method, EUV light with extremely high power is necessary in order to generate hydrogen radicals, and thus it has been difficult to employ this method for an inspection apparatus for masks with a power of EUV light that is low by an order(s) of magnitude.

The present invention has been made to solve such problems, and an object of the present invention is to provide a mask inspection apparatus and a mask inspection method that can prevent a reduction in a reflectance of a drop-in mirror, which is caused by stains such as carbon contaminants or the like, in an Actinic inspection apparatus that uses an EUV light source. Another object of the present invention is to provide a mask inspection apparatus and a mask inspection method that can prevent an interruption of an inspection, which is caused by cleaning of a drop-in mirror.

SUMMARY OF THE INVENTION

A mask inspection apparatus according to the present invention includes a drop-in mirror including: a multi-layer film; and a reflective surface. The drop-in mirror is configured to reflect illumination light incident on the reflective surface and illuminate a mask, an area of the reflective surface is configured to be greater than an area of an illuminated spot irradiated with the illumination light on the reflective surface, the drop-in mirror is configured to be movable, and a position of the illuminated spot on the reflective surface is configured to be moved when the drop-in mirror is moved. With such a configuration, it is possible to prevent a reduction in a reflectance of the drop-in mirror, which is caused by stains such as carbon contaminants or the like.

The drop-in mirror includes a silicon wafer. With such a configuration, it is possible to prevent a local temperature increase and a reduction in a reflectance of the drop-in mirror, which is caused by stains such as carbon contaminants or the like.

The drop-in mirror is configured to be moved while maintaining a central angle of incidence and a central angle of reflection of an optical axis of the illumination light with respect to the reflective surface. With such a configuration, the mask inspection apparatus can be continuously operated without exchanging the drop-in mirror.

The mask inspection apparatus further includes a first concave mirror configured to collect specularly reflected light that is illumination light reflected by the mask, and a second concave mirror configured to collect reflected light from the first convex mirror. A position of the illuminated spot is between the second convex mirror and the mask. With such a configuration, the number of apertures of the projection optical system will be increased. More specifically, the number of apertures for components to be captured in the reflected light from the mask will become large, thereby improving contrast of an image in a bright field observation and thus improving the quality of the image.

A part that was in the illuminated spot on the reflective surface, which has been moved outside the illuminated spot when the drop-in mirror is moved, is configured to be irradiated with cleaning light including VUV light with a wavelength different from a wavelength of the illumination light. With such a configuration, it is possible to prevent a reduction in a reflectance of the drop-in mirror, which is caused by stains such as carbon contaminants or the like.

The drop-in mirror includes a rotation axis, and the drop-in mirror is configured to be rotated around the rotation axis. With such a configuration, the mask inspection apparatus can be continuously operated without exchanging the drop-in mirror.

The drop-in mirror is configured to be extended in a direction vertical to a surface including an optical axis of the illumination light incident on the reflective surface and an optical axis of the illumination light reflected by the reflective surface, and the drop-in mirror is configured to be moved in the direction vertical to the surface. With such a configuration, the mask inspection apparatus can be continuously operated without exchanging the drop-in mirror.

A mask inspection apparatus according to the present invention including a drop-in mirror including: a multi-layer film; and a reflective surface. The drop-in mirror is configured to reflect illumination light incident on the reflective surface and illuminate a mask, an area of the reflective surface is configured to be greater than an area of an illuminated spot irradiated with the illumination light on the reflective surface, the drop-in mirror is configured to be movable, a position of the illuminated spot on the reflective surface is configured to be moved when the drop-in mirror is moved, and a part that was in the illuminated spot on the reflective surface, which has been moved outside the illuminated spot, is configured to be irradiated with cleaning light with a wavelength different from a wavelength of the illumination light. With such a configuration, it is possible to prevent an interruption of an inspection, which is caused by cleaning of a drop-in mirror.

The mask inspection apparatus further includes: a light source configured to generate light comprising EUV light and DUV light; and a diffraction grating configured to disperse the light into the illumination light comprising the EUV light and the cleaning light comprising the DUV light. With such a configuration, it is possible to prevent a reduction in a reflectance of the drop-in mirror, which is caused by stains such as carbon contaminants or the like.

Further, the drop-in mirror is configured to be disposed in an apparatus exhausted by a vacuum pump. With such a configuration, the quantity of the reflected light can be increased, contrast of an image in a bright field observation can be improved, and thus the quality of the image can be improved.

The mask inspection apparatus further includes a condenser lens configured to collect the cleaning light on the part. With such a configuration, stains such as carbon contaminants or the like on the drop-in mirror can be evenly decomposed and removed.

A mask inspection method according to the present invention using a drop-in mirror including a multi-layer film and a reflective surface includes: reflecting illumination light incident on the reflective surface and illuminating a mask; making an area of the reflective surface be greater than an area of an illuminated spot that is a part of the reflective surface irradiated with the illumination light; allowing the drop-in mirror to be movable; and moving the drop-in mirror in order to move a position of the illuminated spot on the reflective surface. With such a configuration, it is possible to prevent a reduction in a reflectance of the drop-in mirror, which is caused by stains such as carbon contaminants or the like.

A part that was in the illuminated spot on the reflective surface, which has been moved outside the illuminated spot when the drop-in mirror is moved, is irradiated with cleaning light with a wavelength different from a wavelength of the illumination light. With such a configuration, it is possible to prevent a foreign matter adhered to an edge of a mask from absorbing the illumination light for inspection and being scattered in the surroundings.

According to the present invention, it is possible to provide a mask inspection apparatus and a mask inspection method that can prevent a reduction in a reflectance of a drop-in mirror, which is caused by stains such as carbon contaminants or the like. It is further possible to provide a mask inspection apparatus and a mask inspection method that can prevent an interruption of an inspection, which is caused by cleaning of a drop-in mirror.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

Hereinafter, a specific configuration of this exemplary embodiment will be described with reference to the drawings. The following descriptions show preferred exemplary embodiments of the present invention, and the scope of the present invention is not limited to the following exemplary embodiments. In the following descriptions, elements denoted by the same reference signs indicate substantially similar elements.

First Exemplary Embodiment

Figure 1A:
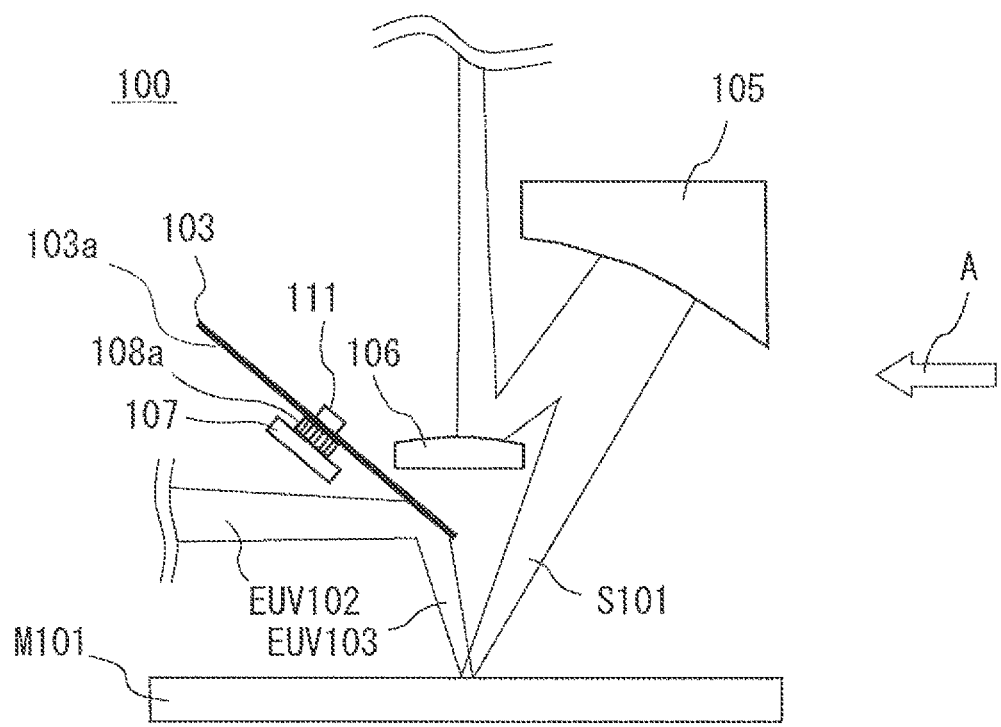
FIG. 1A is a cross-sectional diagram showing an example of a mask inspection apparatus according to a first exemplary embodiment.

This exemplary embodiment relates to an exemplary embodiment of a mask inspection apparatus. Firstly, a configuration of the mask inspection apparatus according to this exemplary embodiment will be described. FIG. 1A is a cross-sectional diagram showing an example of the mask inspection apparatus according to a first exemplary embodiment, and FIG. 1B is a drawing in which the mask inspection apparatus is seen from a direction A in FIG. 1A.

Figure 1B:
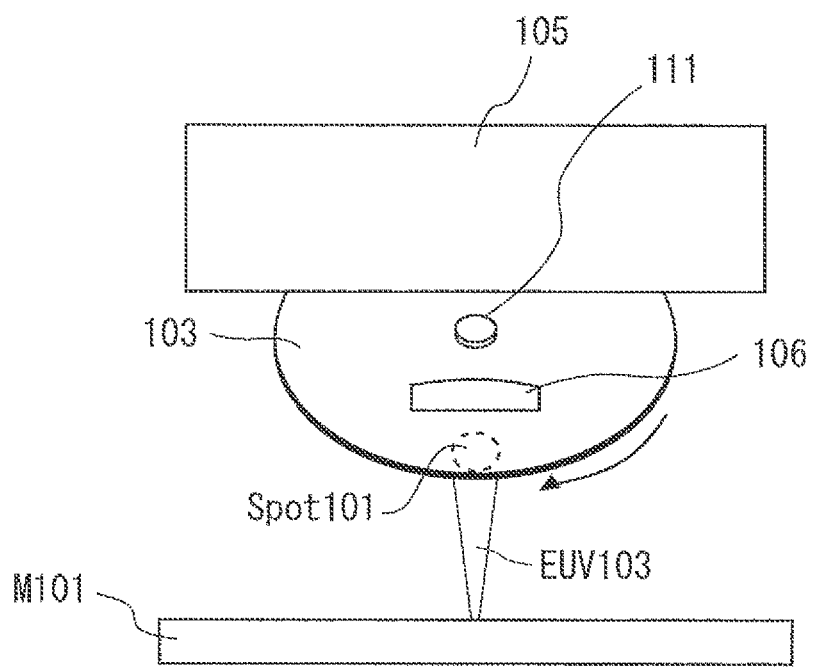
FIG. 1B is a drawing showing the example of the mask inspection apparatus according to the first exemplary embodiment and is a drawing in which the mask inspection apparatus is seen from a direction A in FIG. 1A.
Figure 10:
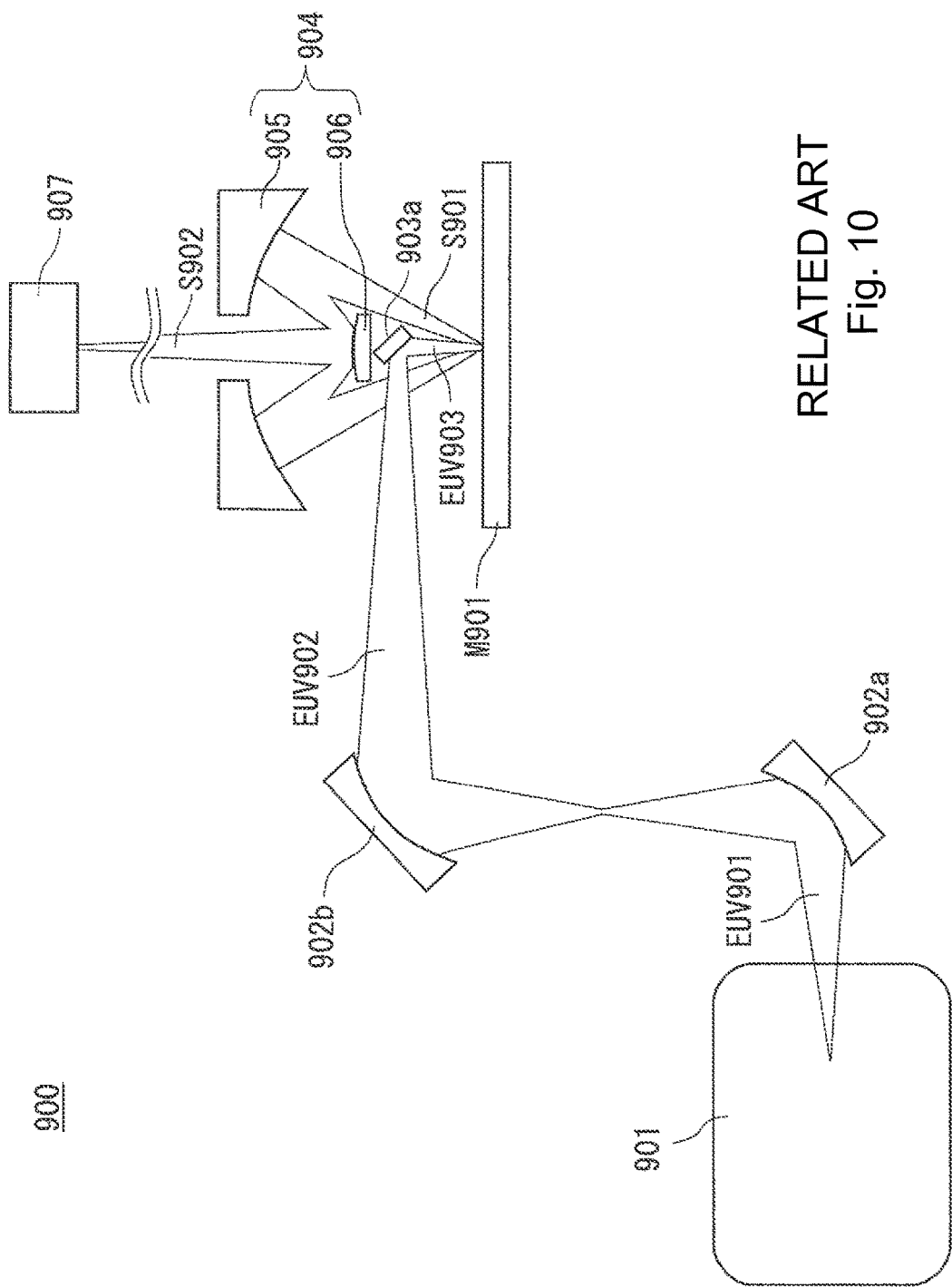
FIG. 10 is a drawing showing an example of a basic configuration of an optical system of an ABI apparatus used in a dark field inspection according to related art.
Figure 11:
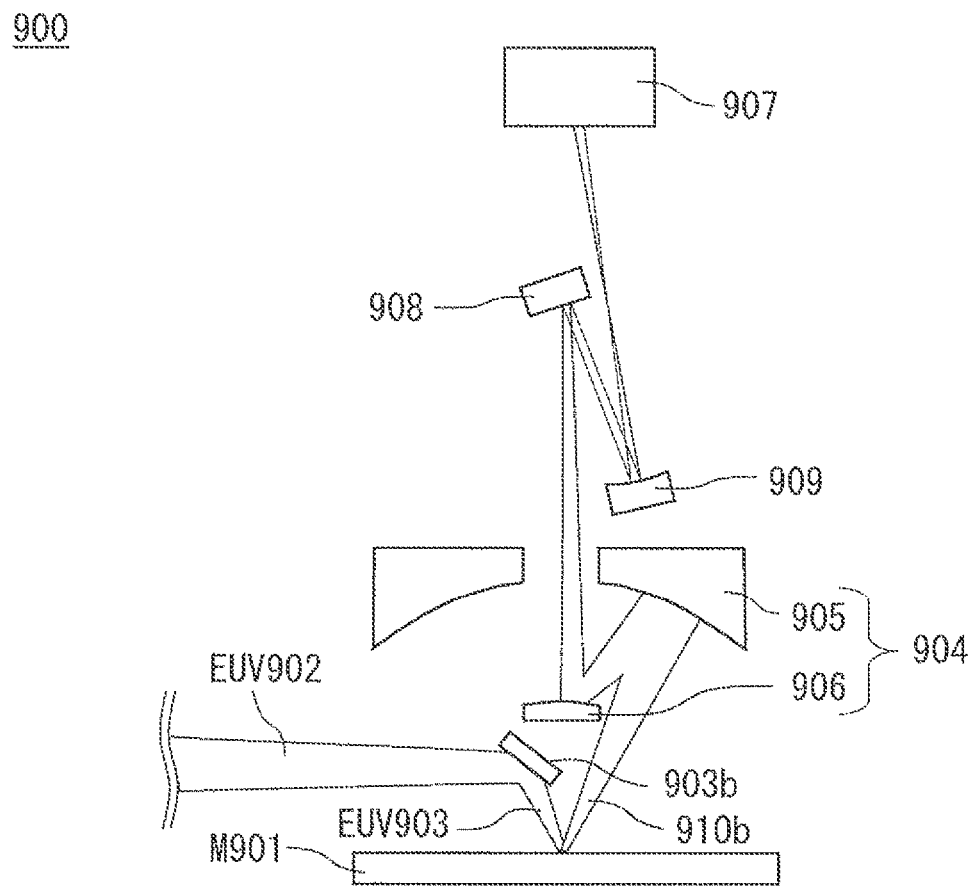
FIG. 11 is a drawing showing an example of a basic configuration of an optical system of an ABI apparatus used in a bright field inspection according to the related art.

As shown in FIGS. 1A and 1B, a mask inspection apparatus 100 includes a drop-in mirror 103, a concave mirror 105, and a convex mirror 106. The mask inspection apparatus 100 further includes an EUV light source, a CCD (Charge Coupled Device) detector, and other optical elements, which are not shown. As the configuration including the EUV light source shown in FIGS. 1A and 1B except for the optical elements is the same as the configuration of the ABI apparatus 900 shown in, for example, FIGS. 10 and 11, it is not shown in FIGS. 1A and 1B. The optical elements including the drop-in mirror 103 are preferably disposed inside an apparatus that has been exhausted by a vacuum pump.

A mask M101 is, for example, an EUV mask. The mask M101 includes an absorber formed on a substrate with a multi-layer film interposed therebetween. The absorber is formed by, for example, depositing tantalum boron nitride (TaBN). The absorber is formed in a pattern by a resist process using EUVL. Accordingly, the mask M101 includes an absorber in which a pattern is formed by EUVL. The mask M101 is placed on a stage (not shown) of the mask inspection apparatus 100.

The drop-in mirror 103 is disposed above the mask M101. The drop-in mirror 103 is, for example, a discoid member with a diameter of 200 mm and a thickness of about 0.75 mm. The drop-in mirror 103 includes a substrate and a multi-layer film. The substrate is, for example, a silicon wafer. The multi-layer film is formed on the substrate. The multi-layer film is, for example, a Mo/Si multi-layer film. The multi-layer film reflects EUV light. A surface of the drop-in mirror 103 on which the multi-layer film is formed is a reflective surface 103a on which illumination light is reflected. Thus, the drop-in mirror 103 includes the reflective surface 103a on which the multi-layer film is provided. The drop-in mirror 103 is disposed in such a way that the reflective surface 103a faces the mask M101 side, for example, disposed downward. The drop-in mirror 103 is inclined toward a mask surface of the mask M101 in such a way that the drop-in mirror 103 reflects illumination light incident on the reflective surface 103a and illuminates the mask M101.

Figure 2:
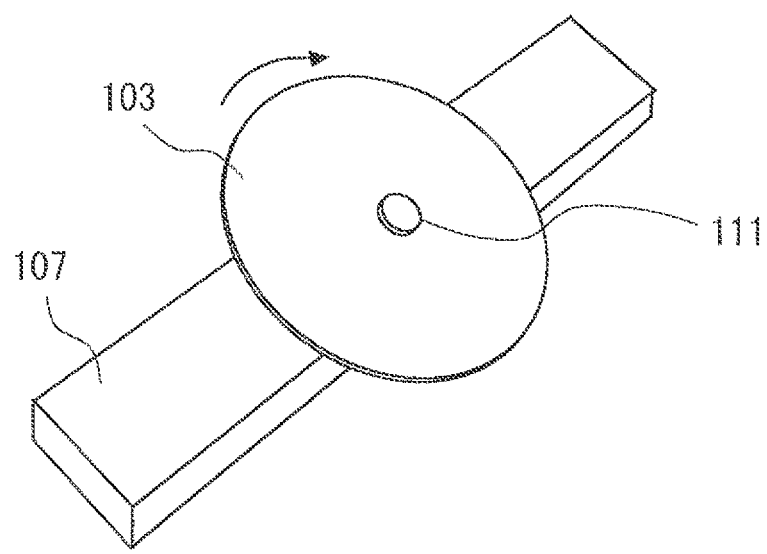
FIG. 2 is a perspective view showing an example of a holding plate of a drop-in mirror according to the first exemplary embodiment.

FIG. 2 is a perspective view showing an example of a holding plate of the drop-in mirror according to the first exemplary embodiment. As shown in FIGS. 1A, 1B, and 2, there is a hole in the drop-in mirror 103 through which a central part of the drop-in mirror 103 is to be penetrated by a rotation axis 111. A cylindrical gear 108a is fixed to the reflective surface 103a side of the drop-in mirror 103 to surround the hole. The hole of the drop-in mirror 103 communicates with an inside of the cylinder of the gear 108a. A holding plate 107 is disposed on the reflective surface 103a side of the drop-in mirror 103. The rotation axis 111 is fixed to the drop-in mirror 103 side of the holding plate 107. The cylindrical gear 108a and the hole of the drop-in mirror 103 are engaged with the rotation axis 111 that is fixed to the holding plate 107. Thus, the drop-in mirror 103 and the gear 108a include the rotation axis 111, and the drop-in mirror 103 and the gear 108a are rotated around the rotation axis 111.

Figure 3:
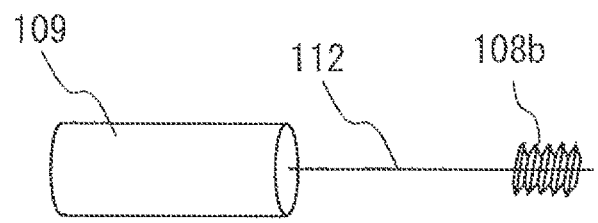
FIG. 3 is a perspective view showing an example of a motor that rotates the drop-in mirror according to the first exemplary embodiment.

FIG. 3 is a perspective view showing an example of a motor that rotates the drop-in mirror according to the first exemplary embodiment. As shown in FIG. 3, the motor 109 includes a rotating rod 112, and a gear 108b is attached to near a distal end of the rotating rod 112. The gear 108b is made to engage with the gear 108a that is fixed to the drop-in mirror 103. With such a configuration, the drop-in mirror 103 can be rotated by the rotation of the motor 109. For example, the drop-in mirror 103 can be rotated while maintaining a central angle of incidence and a central angle of reflection of an optical axis of illumination light EUV102 with respect to the reflective surface 103a.

As shown in FIGS. 1A and 1B, the concave mirror 105 is disposed to face the mask surface side of the mask M101 and be distant from the mask surface of the mask M101. A reflective surface of the concave mirror 105 faces the mask M101 side. The convex mirror 106 is disposed between the concave mirror 105 and the mask M101. A reflective surface of the convex mirror 106 faces the concave mirror 105 side. A part of the reflective surface 103a of the drop-in mirror 103 is disposed between the convex mirror 106 and the mask M101.

Next, an operation of the EUV mask inspection apparatus 100 according to this exemplary embodiment will be described. As shown in FIGS. 1A and 1B, the illumination light EUV102 is emitted from an EUV light source (not shown). The illumination light EUV102 includes, for example, EUV light. The emitted illumination light EUV102 is incident on the reflective surface 103a of the drop-in mirror 103, for example, near a peripheral edge of the reflective surface 103a, which is a side closer to the mask M101. The drop-in mirror 103 reflects the incident illumination light EUV102 by the reflective surface 103a and illuminates the mask M101. That is, illumination light EUV103 reflected by the reflective surface 103a travels towards the mask M101.

A central angle of incidence of the illumination light EUV103 with respect to the mask M101 is, for example, 6 degrees. Specularly reflected light S101 travelling from a part of the mask M101 illuminated by the illumination light EUV103 is reflected by the concave mirror 105 and the convex mirror 106 that constitute a Schwarzschild optical system and then incident on the CCD detector (not shown).

A part of the reflective surface 103a of the drop-in mirror 103 on which the illumination light EUV102 is incident will be referred to as an illuminated spot Spot101. An area of the reflective surface 103a is greater than that of the illuminated spot Spot101. The area of the illuminated spot Spot101 is small, about 1 cm². Therefore, an intensity of light on the illuminated spot Spot101 is high, and thus the generation speed of stains on this spot such as carbon contaminants is fast. Accordingly, during an inspection, stains (carbon contaminants) containing carbon compounds are formed on the illuminated spot Spot101. Thus, the reflectance of the reflective surface 103a of the drop-in mirror 103 is reduced. More specifically, the reflectance could be reduced by about 0.5% by one-hour of EUV irradiation. For example, an inspection for 24 hours a day causes about a 10% reduction in the reflectance.

In order to prevent this reduction, in this exemplary embodiment, the drop-in mirror 103 is rotated, for example, once a day by a predetermined angle. To be more specific, the drop-in mirror 103 is rotated in such a way that the position of the illuminated spot Spot101 is shifted by about 1 cm. By doing so, the illuminated spot Spot101 on the reflective surface 103a is completely moved from the previous spot in one rotation.

As described above, in this exemplary embodiment, the drop-in mirror 103 is movable. A movement of the drop-in mirror 103 moves the position of the illuminated spot Spot101 on the reflective surface 103a. In addition, the drop-in mirror 103 can be moved while maintaining the central angle of incidence and the central angle of reflection of the optical axis of the illumination light EUV102 with respect to the reflective surface 103a.

In the mask inspection apparatus 100 according to this exemplary embodiment, the drop-in mirror 103 is rotatably attached. With such a configuration, the drop-in mirror 103 is rotated before the reduction in the reflectance exerts an influence on the inspection even when stains such as carbon contaminants or the like is formed on the illuminated spot Spot101 on the reflective surface 103a of the drop-in mirror 103. Thus, the position of the illuminated spot Spot101 with the reduced reflectance can be moved.

Further, the drop-in mirror 103 can be moved while maintaining the central angle of incidence and the central angle of reflection of the optical axis of the illumination light with respect to the reflective surface 103a. It is thus possible to move the drop-in mirror 103 while continuing the inspection. Moreover, the mask inspection apparatus 100 can be continuously operated without exchanging the drop-in mirror 103 for a long period.

To be more specific, the illuminated spot Spot101 is located at a position about 95 mm from the center of the discoid drop-in mirror 103. Thus, the lengths of parts that can be used as the illuminated spot Spot101 are each about 60 cm around an entire circumference of the drop-in mirror 103. Accordingly, the drop-in mirror 103 can be rotated about 60 times. When the mask inspection apparatus 100 is continuously operated, the drop-in mirror 103 can be rotated once a day. Thus, the mask inspection apparatus 100 can be continuously operated for about two months without exchanging the drop-in mirror 103 for about two months.

The above discoid drop-in mirror 103 uses, for example, an eight inches silicon wafer as a substrate. A commercial silicon wafer with a diameter of 200 mm or 300 mm is available to be used in manufacturing a semiconductor, the surfaces of which are extremely flat and have an extremely low roughness. It is thus easy to manufacture a multi-layer mirror for EUV that includes a silicon wafer as a substrate.

The thermal conductivity of silicon (Si) is 149 W/mK and is greater than the thermal conductivity of synthetic quarts, 1.38 W/mK, which is a common substrate material for mirrors, by two orders of magnitude. Accordingly, when the part of the illuminated spot Spot101 illuminated by the illumination light is heated by the absorption of the EUV light, the heat is immediately conducted to other parts thereof. It is thus possible to prevent a local temperature increase. As the temperature increase of the multi-layer film on the illuminated spot Spot101 can be prevented, it is possible to reduce a shift in an optimum reflected wavelength caused by a thermal expansion of the multi-layer film to an ignorable level. Accordingly, a high reflectance can be maintained at a design wavelength of the multi-layer film, which is 13.5 nm. A multi-layer mirror for EUV that uses a commercial silicon wafer as a substrate is disclosed by, for example, Satoshi Ichimaru, et al, "Mo/Si multi-layer mirrors with 300-bilayers for EUV lithography," SPIE Vol. 9658, 965814 (2015).

On the other hand, as an area of the drop-in mirror 103 including the silicon wafer is greater than those of the drop-in mirrors 903a and the like of the ABI apparatus 900 according to the related art, the entire drop-in mirror 103 cannot be disposed under the convex mirror 106 that constitutes the Schwarzschild optical system. However, in a bright field inspection, even when a part of the drop-in mirror 103 is extended beyond one side of the convex mirror 106, the specularly reflected light that is reflected from the mask M101 and travels toward the other side of the convex mirror 106 will not be blocked. Accordingly, as in this exemplary embodiment, the drop-in mirror 103 including a silicon wafer as a substrate can be used.

Modified Example

Figure 4A:
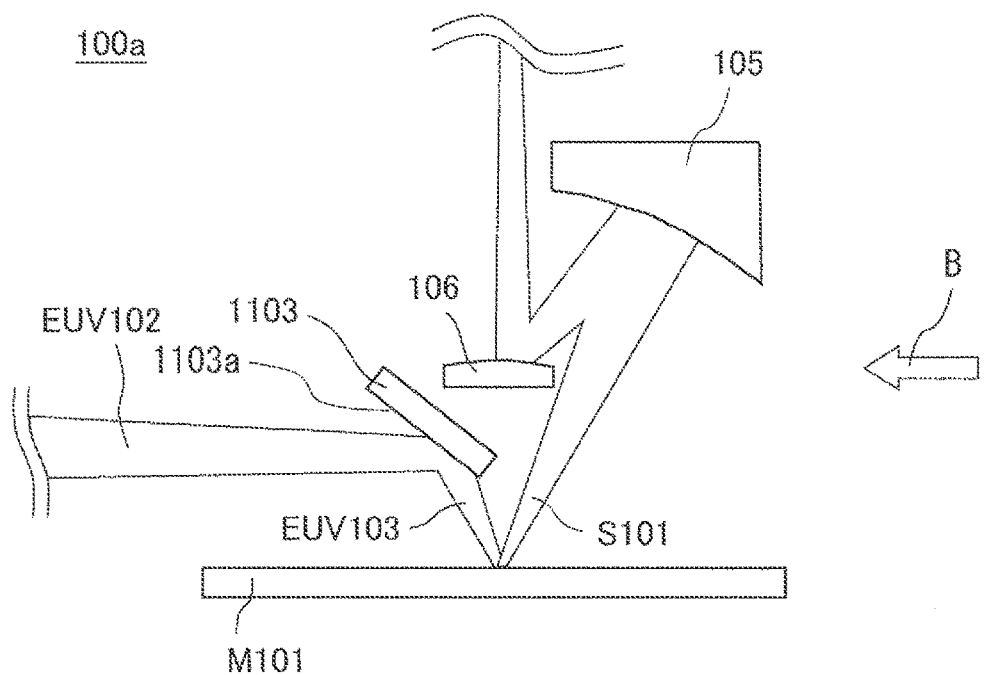
FIG. 4A is a cross-sectional diagram showing an example of a mask inspection apparatus according to a modified example of the first exemplary embodiment.

Next, a mask inspection apparatus according to a modified example of the first exemplary embodiment will be described. FIG. 4A is a cross-sectional diagram showing an example of the mask inspection apparatus according to the modified example of the first exemplary embodiment, and FIG. 4B is a drawing in which the mask inspection apparatus is seen from a direction B in FIG. 4A.

Figure 4B:
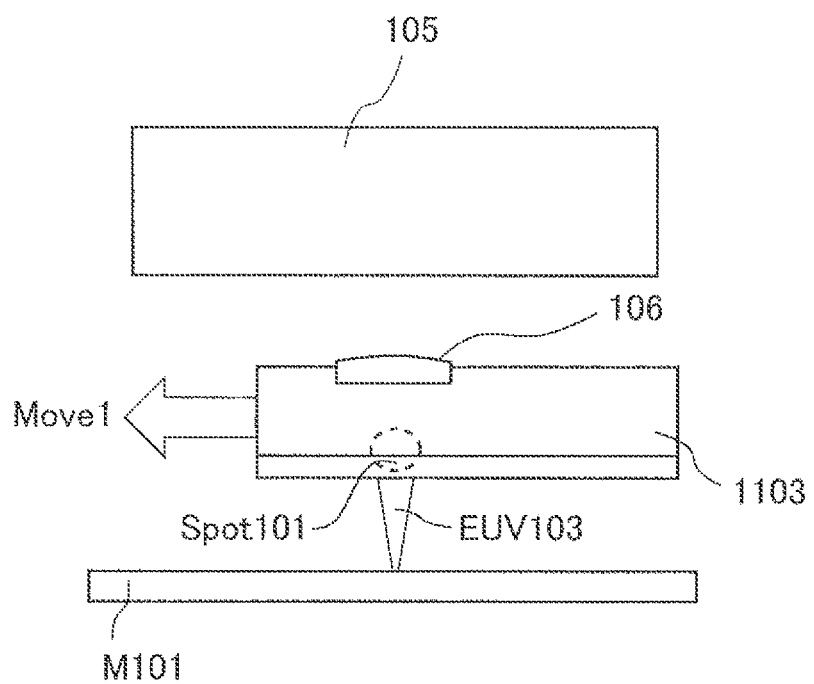
FIG. 4B is a drawing showing an example of the mask inspection apparatus according to the modified example of the first exemplary embodiment and is a drawing in which the mask inspection apparatus is seen from a direction B in FIG. 4A.

As shown in FIGS. 4A and 4B, a drop-in mirror 1103 of a mask inspection apparatus 100a is a plate-like member that is extended in a direction vertical to a surface including an optical axis of the illumination light EUV102 that is incident on the reflective surface 1103a and an optical axis of the illumination light EUV103 that is reflected by the reflective surface 1103a. The drop-in mirror 1103 can be moved in the direction in which the drop-in mirror 1103 is extended.

As shown in FIGS. 4A and 4B, the mask inspection apparatus 100a includes the drop-in mirror 1103, the concave mirror 105, and the convex mirror 106. The mask inspection apparatus 100a further includes an EUV light source, a CCD (Charge Coupled Device) detector, and other optical elements, which are not shown. As the configuration including the EUV light source shown in FIGS. 4A and 4B except for the optical elements is the same as the configuration of the ABI apparatus 900 shown in, for example, FIGS. 10 and 11, it is not shown in FIGS. 4A and 4B. The optical elements including the drop-in mirror 1103 are preferably disposed inside an apparatus that has been exhausted by a vacuum pump.

The drop-in mirror 1103 is disposed above the mask M101. The drop-in mirror 1103 is, for example, a plate-like member that is extended in one direction. The drop-in mirror 1103 includes a substrate and a multi-layer film. The substrate is, for example, a low thermal expansion glass. The multi-layer film is formed on the substrate. The multi-layer film is, for example, a Mo/Si multi-layer film.

The drop-in mirror 1103 is extended in a direction vertical to a surface including an optical axis of the illumination light EUV102 that is incident on the reflective surface 1103a and an optical axis of the illumination light EUV103 that is reflected by the reflective surface 1103a. The drop-in mirror 1103 can be slid in a direction Move1 in which the drop-in mirror 1103 is extended by a motor or the like (not shown). Thus, the drop-in mirror 1103 can be moved while maintaining the central angle of incidence and the central angle of reflection of the optical axis of the illumination light EUV102 with respect to the reflective surface 1103a.

As shown in FIGS. 4A and 4B, the concave mirror 105 is disposed to face the mask surface side of the mask M101 and be distant from the mask surface of the mask M101. The reflective surface of the concave mirror 105 faces the mask M101 side. The convex mirror 106 is disposed between the concave mirror 105 and the mask M101. A reflective surface of the convex mirror 106 faces the concave mirror 105 side. A part of the reflective surface 1103a of the drop-in mirror 1103 is disposed between the convex mirror 106 and the mask M101.

In this modified example, the drop-in mirror 1103 is slid a predetermined distance, for example, once a day in a direction indicated by the direction Move1. To be more specific, the drop-in mirror 1103 is slid in such a way that the position of the illuminated spot Spot101 is shifted by about 1 cm. Thus, the illuminated spot Spot101 is completely moved from the previous spot in one slide.

A silicon wafer that has been cut into a plate-like shape may be used as a substrate of the drop-in mirror 1103. Other configurations, operations, and advantages of the modified example are the same as those described in the first exemplary embodiment.

Second Exemplary Embodiment

Figure 5:
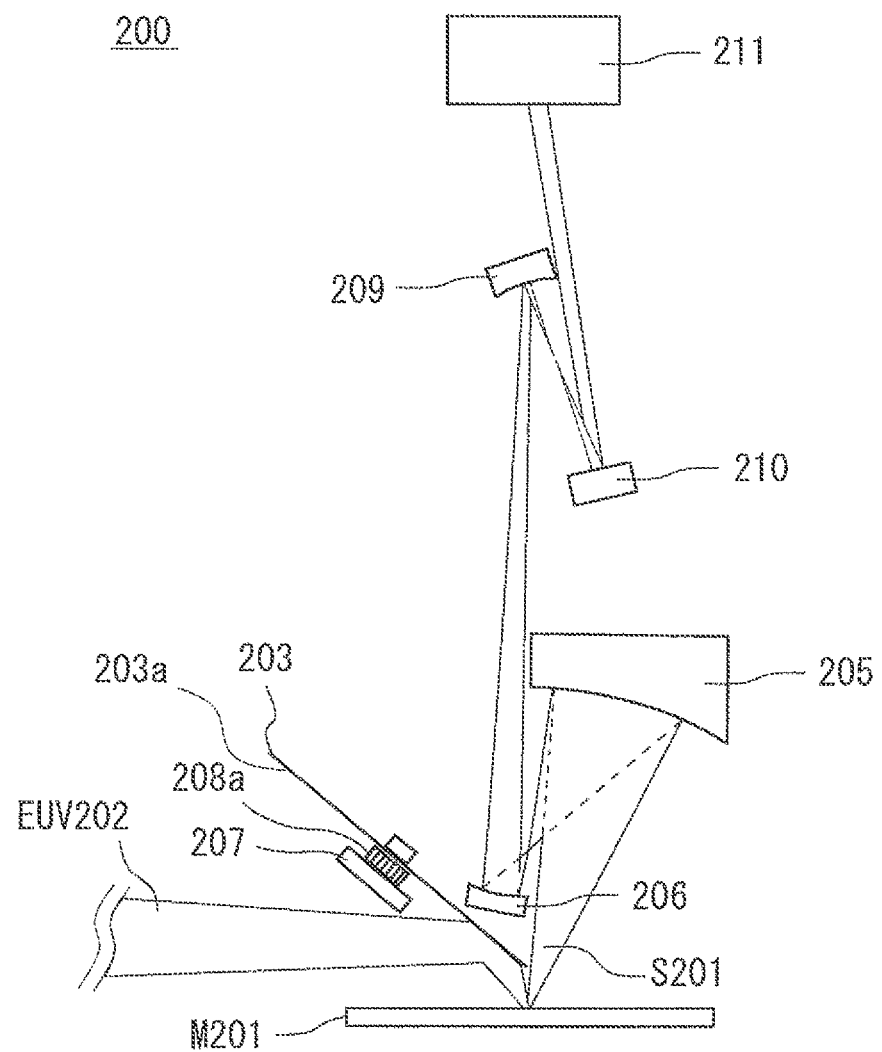
FIG. 5 is a cross-sectional diagram showing a mask inspection apparatus according to a second exemplary embodiment.

Next, a mask inspection apparatus according to a second exemplary embodiment will be described. FIG. 5 is a cross-sectional diagram showing the mask inspection apparatus according to the second exemplary embodiment. As shown in FIG. 5, a mask inspection apparatus 200 is for inspecting a mask M201. The mask inspection apparatus 200 is a projection optical system that includes four multi-layer mirrors in total, which are: a concave mirror 205 (a first concave mirror), a concave mirror 206 (a second concave mirror), a concave mirror 209, and a planar mirror 210. The mask inspection apparatus 200 further includes other optical elements, which are: a drop-in mirror 203, a CCD detector 211, a light source (not shown), and optical elements that constitute an illumination optical system (not shown).

The concave mirror 205 is disposed to face the mask surface side of the mask M201 and be distant from the mask surface. A reflective surface of the concave mirror 205 faces the mask M201 side. The concave mirror 206 is disposed between the concave mirror 205 and the mask M201. A reflective surface of the concave mirror 206 faces the concave mirror 205 side. A part of the reflective surface 203a of the drop-in mirror 203 is disposed between the concave mirror 206 and the mask M201. The concave mirror 209 is disposed above the concave mirror 205. A reflective surface of the concave mirror 209 faces the concave mirror 206 side. The planar mirror 210 is disposed between the concave mirrors 205 and 209. A reflective surface of the planar mirror 210 faces the concave mirror 209 and the CCD detector 211.

The concave mirror 205 collects specularly reflected light S201 from the mask M201, which is reflected light of illumination light EUV202. The concave mirror 206 inverts and collects reflected light from the concave mirror 205. The concave mirror 209 collects specularly reflected light from the concave mirror 206. The planar mirror 210 reflects specularly reflected light from the concave mirror 209. Thus, an inspection can be performed with a high magnification of about 400 times. In order for the EUV light with sufficient power to travel from the mask M201 to reach the CCD detector 211, power of the illumination light EUV202 is made to be greater than that of the illumination light in the ABI apparatus 900 according to the related art by one to two orders of magnitude. For example, the power of the illumination light EUV202 is an average of several tens of milliwatts.

In this exemplary embodiment, in a manner similar to the mask inspection apparatus 100 shown in FIGS. 1A and 1B, the discoid drop-in mirror 203 including a silicon wafer as a substrate is used. Thus, the position of the illuminated spot on the reflective surface 203a is moved when the drop-in mirror 203 is moved.

This exemplary embodiment takes advantage of the thickness of the drop-in mirror 203. The thickness of the silicon wafer of the substrate of the drop-in mirror 203 is about 0.75 mm. As compared to a common mirror substrate for a laser, a thickness of which is 5 to 10 mm, the silicon wafer of the substrate of the drop-in mirror 203 is extremely thin. As a result, the second multi-layer mirror of the four multi-layer mirrors that constitute the projection optical system, namely, the concave mirror 206 in FIG. 5, can be disposed at a low position to be close to the mask M201. Accordingly, the concave mirror 206 can invert and collect reflected light that has been reflected by the concave mirror 205. As the second multi-layer mirror is the concave mirror 206, the number of apertures of the projection optical system will be increased. More specifically, the number of apertures for components to be captured in the reflected light from the mask will become large, thereby improving contrast of an image in a bright field observation and thus improving the quality of the image.

Figure 6A:
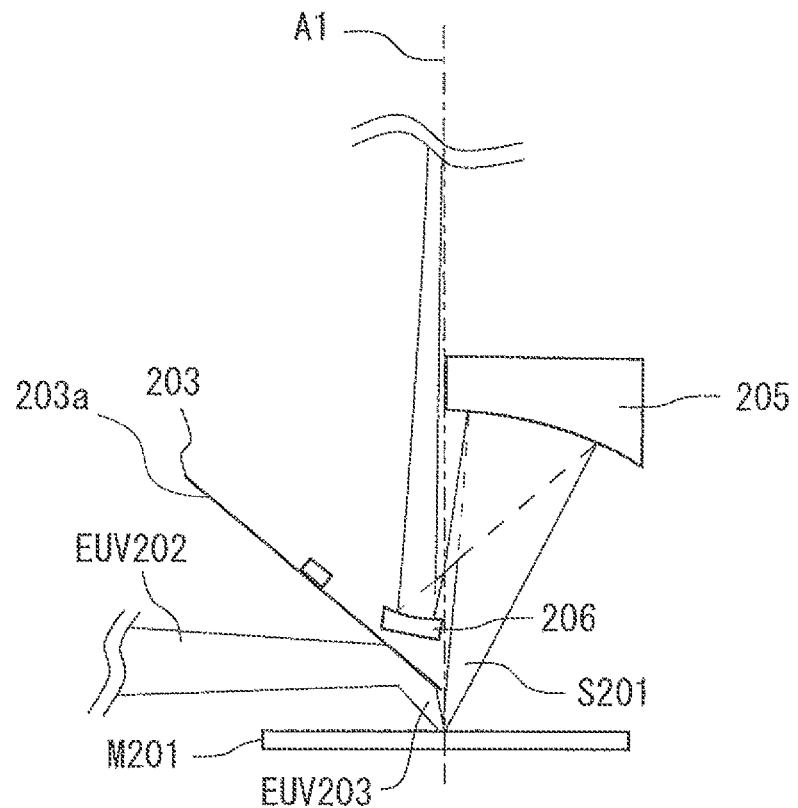
FIG. 6A is a drawing showing an example of a part of an optical system of the mask inspection apparatus according to the second exemplary embodiment.
Figure 6B:
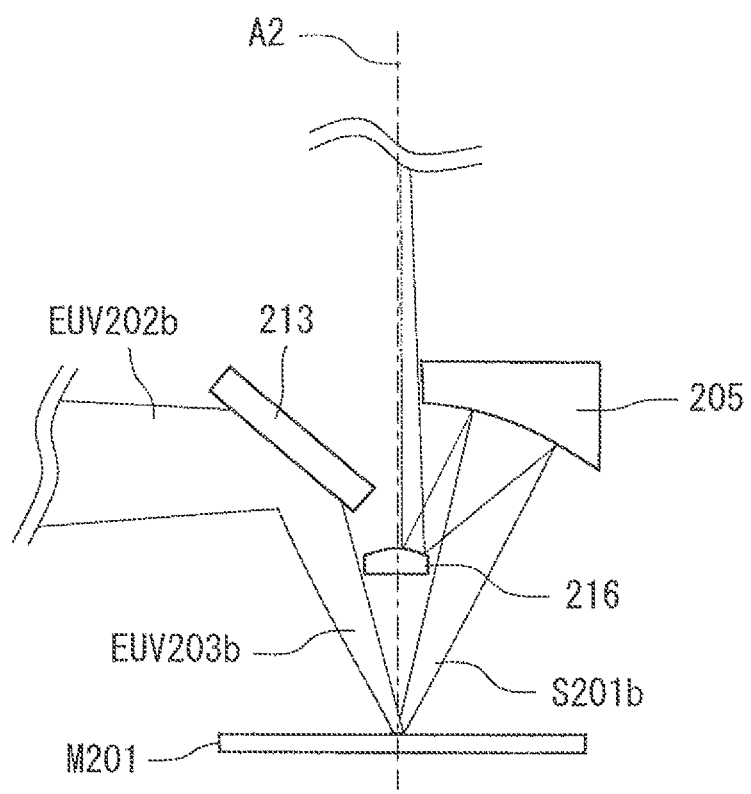
FIG. 6B is a drawing showing an example of a part of an optical system of an inspection apparatus according to related art.

FIG. 6A is a drawing showing an example of a part of the optical system of the mask inspection apparatus according to the second exemplary embodiment, and FIG. 6B is a drawing showing an example of a part of an optical system of a mask inspection apparatus according to related art.

As shown in FIG. 6B, in the inspection apparatus according to the related art, the drop-in mirror 213 is disposed at a high position distant from the mask M201 in such a way that illumination light EUV203b that illuminates the mask M201 will not be shielded by the convex mirror 216. In this way, an area of an illuminated spot illuminated by the illumination light EUV202b that is incident on the drop-in mirror 213 can be increased. Accordingly, an intensity of the EUV light on the drop-in mirror 213 can be reduced, and thus it is difficult for stains such as carbon contaminants to be formed thereon. However, in such a case, a part of the convex mirror 216 on which specularly reflected light S201b generated from the mask M201 will be incident will become a half of the convex mirror 216 that is on the opposite side of the drop-in mirror 213 with respect to an optical axis A2. Therefore, the quantity of the reflected light is reduced.

On the other hand, in the mask inspection apparatus 200 according to this exemplary embodiment shown in FIG. 6A, the second multi-layer film is the concave mirror 206. Accordingly, the specularly reflected light S201 is incident on the concave mirror 206 that is disposed on a side closer to the drop-in mirror 203 with respect to an optical axis A1. That is, the specularly reflected light S201 is made to travel at a large solid angle to become close to the optical axis A1. However, in order to do so, a solid angle of the illumination light EUV203 that illuminates the mask M201 is increased, and thus the illumination light EUV203 will also become closer to the optical axis A1. Accordingly, the drop-in mirror 203 needs to be disposed at a position lower than the concave mirror 206. The illuminated spot on the reflective surface 203a of the drop-in mirror 203 is positioned between the concave mirror 206 (the second convex mirror) and the mask M201.

According to this exemplary embodiment, the silicon wafer used as the substrate of the drop-in mirror 203 contributes to a reduction in the thickness of the drop-in mirror 203. Thus, the concave mirror 206 can be used as the multi-layer mirror that is disposed closest to the mask M201 constituting the magnifying projection optical system. In this way, the number of apertures of the projection optical system will be increased. More specifically, the number of apertures for components to be captured in the reflected light from the mask will become large, thereby improving contrast of an image in a bright field observation and thus improving the quality of the image.

Third Exemplary Embodiment

Figure 7A:
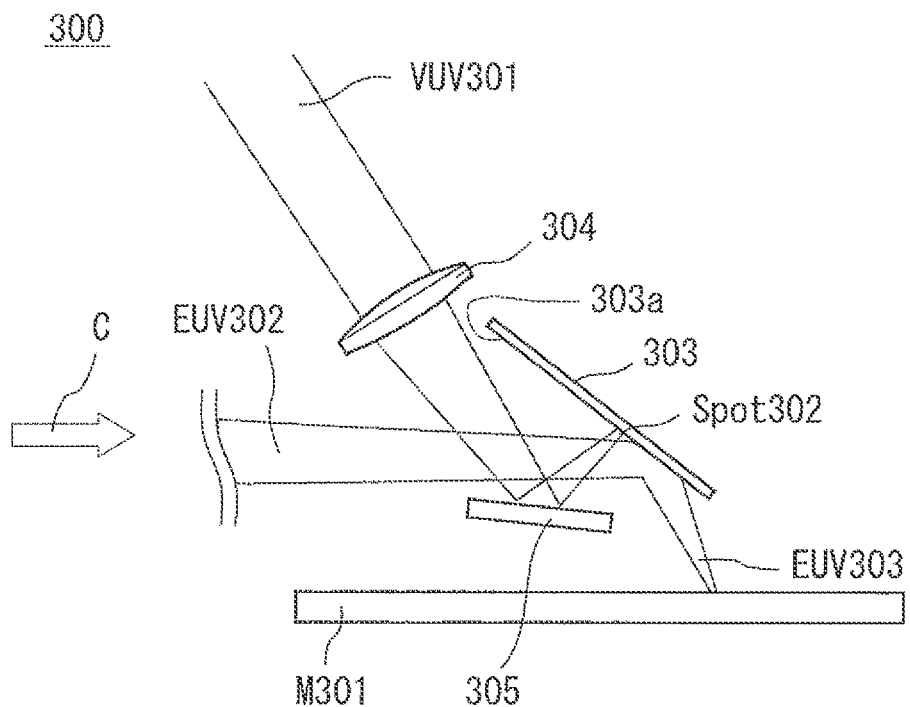
FIG. 7A is a cross-sectional diagram showing an example of a mask inspection apparatus according to a third exemplary embodiment.

Next, a mask inspection apparatus according to a third exemplary embodiment will be described. The mask inspection apparatus according to this exemplary embodiment includes a cleaning mechanism for the drop-in mirror 303. FIG. 7A is a cross-sectional diagram showing an example of the mask inspection apparatus according to the third exemplary embodiment, and FIG. 7B is a drawing in which the mask inspection apparatus is seen from a direction C in FIG. 7A.

Figure 7B:
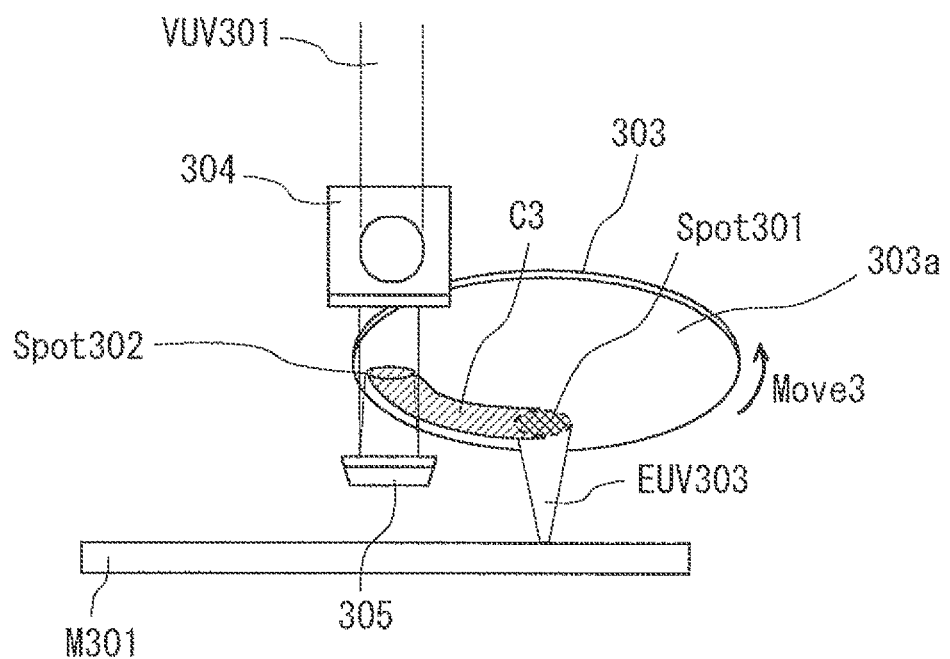
FIG. 7B is a drawing showing an example of the mask inspection apparatus according to the third exemplary embodiment and is a drawing in which the mask inspection apparatus is seen from a direction C in FIG. 7A.

As shown in FIGS. 7A and 7B, the mask inspection apparatus 300 is an apparatus for inspecting a mask M301. The mask inspection apparatus 300 includes a drop-in mirror 303, a cylindrical lens 304, and a mirror 305. The mask inspection apparatus 300 further includes a light source, a light source for cleaning, an illumination optical system, a projection optical system, and a CCD detector, which are not shown.

The mirror 305 is disposed between the drop-in mirror 303 and the mask M301. A reflective surface of the mirror 305 faces a reflective surface 303a side of the drop-in mirror 303. The light source for cleaning generates laser beams including DUV light (Deep UV light), preferably VUV light (Vacuum UV light) with a wavelength of 157 nm. The light source for cleaning is, for example, an $F_2$ laser (a hydrogen fluoride laser) or an ArF excimer laser. A condenser lens, for example, a cylindrical lens 304, is disposed between the mirror 305 and the light source for cleaning.

In the mask inspection apparatus 300, a carbon contaminant C3 is gradually deposited on an illuminated spot Spot301 on the reflective surface 303a by EUV light EUV302 that is incident on the drop-in mirror 303. However, in a manner similar to that of the first exemplary embodiment described with reference to FIGS. 1A and 1B, the drop-in mirror 303 is rotatably attached in this exemplary embodiment. Therefore, when the drop-in mirror 303 is rotated in a direction indicated by a direction Move3, a part where the carbon contaminant C3 is adhered moves outside the illuminated spot Spot301.

On the other hand, the cleaning light VUV301 including the VUV light with a wavelength of 157 nm that is emitted from the laser for cleaning passes through the cylindrical lens 304 and travels while being narrowed in one direction. Then, the cleaning light VUV301 is reflected by the mirror 305 and collected on an elongated region such as an illuminated spot Spot302 on the drop-in mirror 303. In this way, stains such as the carbon contaminant C3 or the like are decomposed and removed.

Note that the light that is incident on the stains such as the carbon contaminant C3 or the like in order to decompose and remove the stains is referred to as cleaning light. Further, DUV light is light with a wavelength of 300 nm or less, and VUV light is light with a wavelength of 200 nm or less.

According to this exemplary embodiment, a part that was in the illuminated spot on the reflective surface 303a of the drop-in mirror 303, which has been moved outside the illuminated spot when the drop-in mirror 303 is moved, is irradiated with the cleaning light including VUV light with a wavelength different from that of the illumination light. Thus, stains such as the carbon contaminant C3 or the like that are formed on the reflective surface 303a can be decomposed and removed, thereby preventing a reduction in the reflectance of the drop-in mirror, which is caused by the stains such as the carbon contaminants or the like.

Further, in a manner similar to that of an exposure apparatus and the like according to the related art, stains such as carbon contaminants or the like can be cleaned without injecting gas such as oxygen, ozone, hydrogen, or the like. It is thus possible to prevent an absorption of the illumination light by gas such as oxygen or the like. Therefore, a reduction in the power of the illumination light can be prevented. Further, an inspection can be performed at the same time as the cleaning, thereby achieving continuous operations for an extremely long period.

Photon energy of the VUV laser beam generated by the ArF excimer laser or the $F_2$ laser is, respectively, 618.6 kJ/mol and 759 kJ/mol, which is high. It is greater than bond-dissociation energy for C—H and C—C in most organic compounds. It is thus possible to decompose and remove stains such as carbon contaminants or the like by the VUV laser beam from the ArF excimer laser or $F_2$ laser.

In particular, as such a VUV laser beam is a pulse laser with high peak power, when the laser beams are collected on the reflective surface, photon density can be extremely high. Accordingly, C—H bonds and C—C bonds in organic compounds can be dissociated. On the other hand, for example, in the cleaning method according to the related art that uses a VUV lamp, it is necessary to introduce oxygen or ozone that absorbs EUV light. Thus, the power of the illumination light is greatly attenuated. For this reason, it is difficult to perform an inspection and cleaning at the same time.

When cleaning is performed using only an $Ar_2$ lamp with a wavelength of 126 nm or an $Xe_2$ lamp with a wavelength of 172 nm without using gas such as oxygen, ozone, or the like, in the method using a lamp, it is necessary to move the lamp extremely close to the multi-layer mirror to be cleaned. For this reason, it is difficult to perform an inspection and cleaning at the same time.

On the other hand, in the present invention, as the laser beam is used for cleaning, only the part where the stains such as carbon contaminants or the like are present on the multi-layer mirror, which is in use, can be selectively irradiated. Therefore, it is possible to irradiate the multi-layer mirror with the laser beam for cleaning in such a way that the illumination light for inspection will not be shielded. Additionally, as the laser beam for cleaning can be collected on a thin linear spot, stains such as carbon contaminants or the like can be evenly decomposed and removed.

According to this exemplary embodiment, stains such as carbon contaminants can be cleaned without injecting gas such as oxygen, ozone, hydrogen, or the like. Therefore, a reduction in the power of the illumination light can be prevented. Further, an inspection can be performed at the same time as the cleaning, thereby achieving continuous operations for an extremely long period. Accordingly, it is possible to prevent an interruption of an inspection, which is caused by cleaning of the drop-in mirror 303.

Fourth Exemplary Embodiment

Figure 8A:
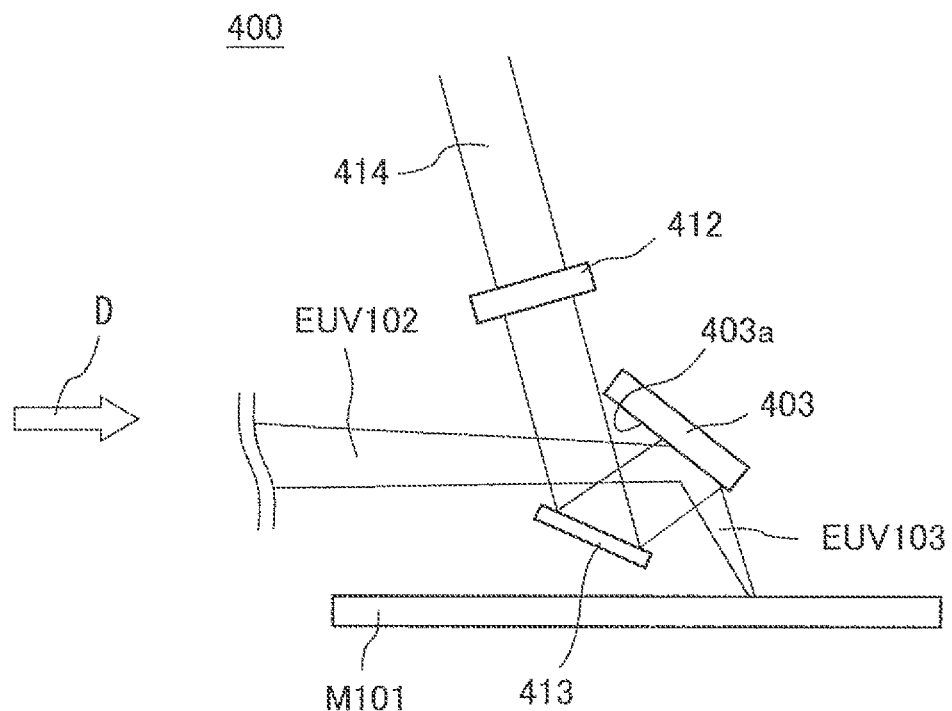
FIG. 8A is a cross-sectional diagram showing an example of a cleaning mechanism of a mask inspection apparatus according to a fourth exemplary embodiment.
Figure 8B:
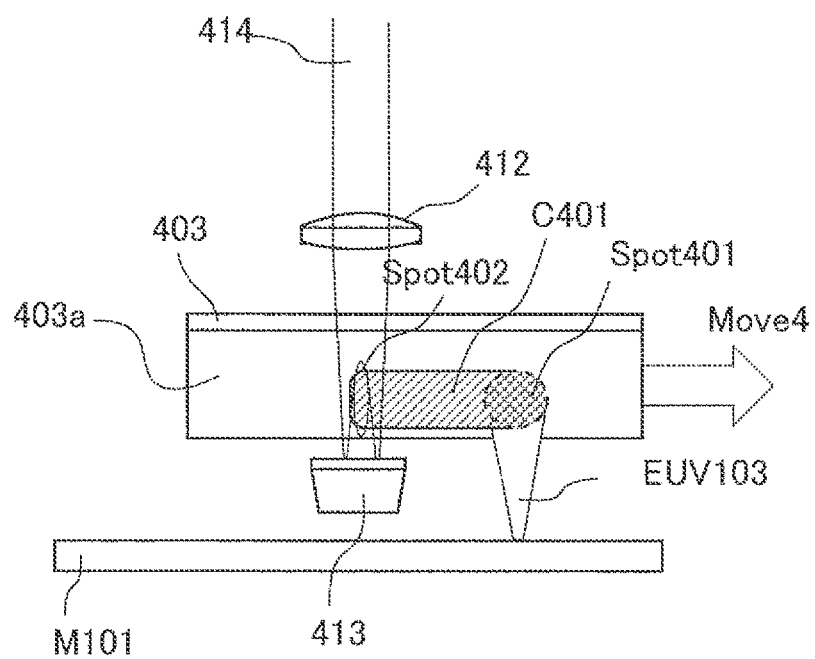
FIG. 8B is a drawing showing an example of the cleaning mechanism of the mask inspection apparatus according to the fourth exemplary embodiment and is a drawing in which the mask inspection apparatus is seen from a direction D in FIG. 8A.

FIG. 8A is a cross-sectional diagram for showing an example of a cleaning mechanism of a mask inspection apparatus according to a fourth exemplary embodiment, and FIG. 8B is a drawing in which the mask inspection apparatus is seen from a direction D in FIG. 8A.

As shown in FIGS. 8A and 8B, a mask inspection apparatus 400 includes a drop-in mirror 403, a concave mirror (not shown), a convex mirror, an EUV light source, a CCD (Charge Coupled Device) detector, and other optical elements. The mask inspection apparatus 400 further includes a cleaning mechanism for removing stains such as carbon contaminants or the like. That is, in addition to a cylindrical lens 412 and a mirror 413, the mask inspection apparatus 400 includes a light source for cleaning (not shown).

The light source for cleaning generates laser beams including DUV light (Deep UV light), preferably VUV light (Vacuum UV light) with a wavelength of 157 nm. The light source for cleaning is, for example, an $F_2$ laser (hydrogen fluoride laser) or an ArF excimer laser. The mirror 413 is disposed between the drop-in mirror 403 and the mask M101. A reflective surface of the mirror 413 faces a reflective surface 403a of the drop-in mirror 403. A condenser lens, for example, a cylindrical lens 412 is disposed between the mirror 413 and the light source for cleaning.

In the mask inspection apparatus 400, stains such as a carbon contaminant C401 or the like are gradually deposited on an illuminated spot Spot401 on the reflective surface 403a by EUV light EUV102 that is incident on the drop-in mirror 403. The drop-in mirror 403 is slidably attached. When the drop-in mirror 403 is slid in a direction indicated by a direction Move4, a part where the carbon contaminant C401 is adhered is moved outside the illuminated spot Spot101.

On the other hand, cleaning light 414 including VUV light with a wavelength 157 nm that is emitted from the laser for cleaning passes through the cylindrical lens 412 and travels while being narrowed in one direction. Then, the cleaning light 414 is reflected by the mirror 413 and collected on an elongated region such as an illuminated spot Spot402 on the drop-in mirror 403. In this way, stains such as the carbon contaminant C401 or the like are decomposed and removed.

Note that the light that is output to stains such as the carbon contaminant C401 or the like in order to decompose and remove the stains is referred to as cleaning light. Further, DUV light is light with a wavelength of 300 nm or less, and VUV light is light with a wavelength of 200 nm or less.

According to this exemplary embodiment, a part that was in the illuminated spot on the reflective surface 403a of the drop-in mirror 403, which has been moved outside the illuminated spot when the drop-in mirror 403 is moved, is irradiated with the cleaning light including light with a wavelength of different from that of the illumination light. Thus, stains such as the carbon contaminant C401 or the like that is formed on the reflective surface 403a can be decomposed and removed, thereby preventing a reduction in the reflectance of the drop-in mirror, which is caused by the stains such as the carbon contaminant C401 or the like. Advantages achieved by this exemplary embodiment other than the above one are the same as those achieved by the third exemplary embodiment.

Fifth Exemplary Embodiment

Figure 9A:
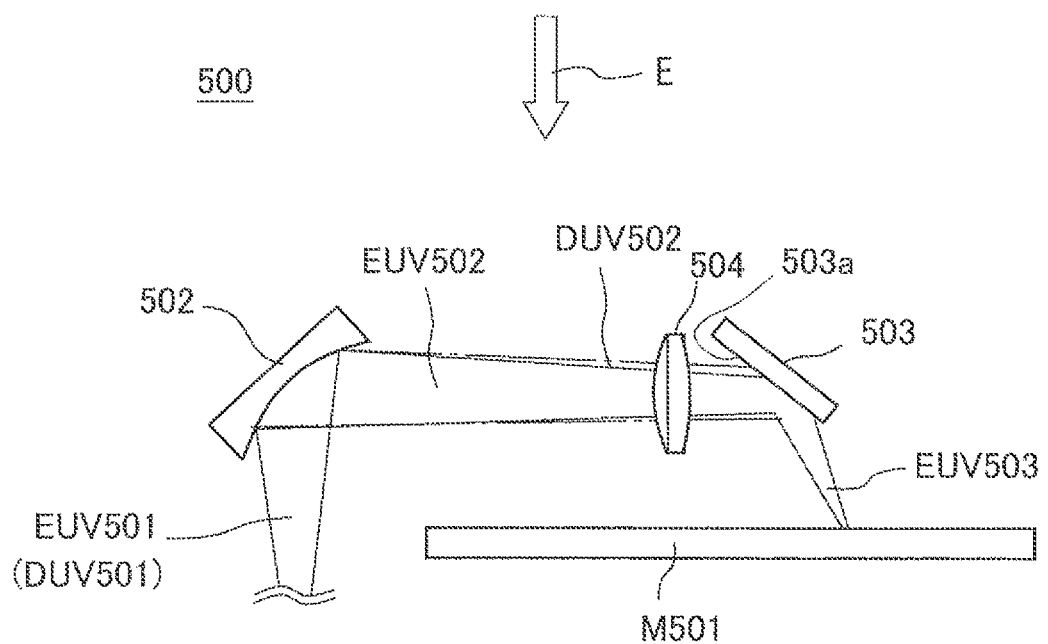
FIG. 9A is a side view showing an example of a part of an optical system of a mask inspection apparatus according to a fifth exemplary embodiment.
Figure 9B:
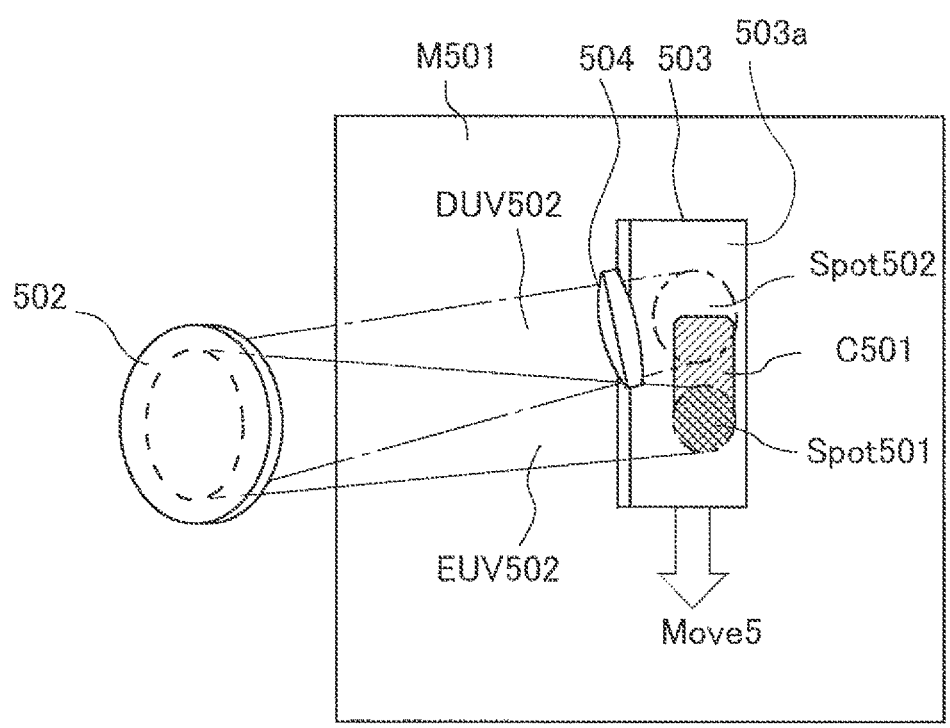
FIG. 9B is a drawing showing an example of the mask inspection apparatus according to the fifth exemplary embodiment and is a drawing in which the mask inspection apparatus is seen from a direction E in FIG. 9A.

Next, an inspection apparatus according to a fifth exemplary embodiment will be described. FIG. 9A is a side view showing an example of a part of an optical system of a mask inspection apparatus according to the fifth exemplary embodiment, and FIG. 9B is a drawing in which the mask inspection apparatus is seen from a direction E in FIG. 9A. As shown in FIGS. 9A and 9B, a mask inspection apparatus 500 includes an ellipsoidal mirror 502, a drop-in mirror 503, and a cylindrical lens 504. The inspection apparatus 500 further includes an EUV light source, an ellipsoidal mirror, and a CCD detector, which are not shown.

The EUV light source generates light including EUV light and DUV light. The light emitted from the EUV light source is reflected by an ellipsoidal mirror (not shown) and is incident on the ellipsoidal mirror 502. The light that is incident on the ellipsoidal mirror 502 includes EUV light and DUV light.

The ellipsoidal mirror 502 is a diffraction grating mirror. The ellipsoidal mirror 502 disperses the EUV light and DUV included in the light into light including the EUV light and light including the DUV light. The ellipsoidal mirror 502 is designed to make DUV light DUV502 of the dispersed light diffracted in a direction different from a direction in which the EUV light EUV502 is diffracted. Therefore, as shown in FIG. 9B, the DUV light DUV502 that has travelled from the ellipsoidal mirror 502 is polarized and then travels in a direction different from a direction in which the EUV light EUV502 is polarized and then travels. As a result, a part that was in the illuminated spot Spot501 on the reflective surface 503a, which has been moved outside the illuminated spot Spot501 when the drop-in mirror 503 is moved, namely, an illuminated spot Spot502, is irradiated with the DUV light DUV502 as cleaning light.

Accordingly, even if stains such as a carbon contaminant C501 or the like are deposited on the drop-in mirror 503, when the drop-in mirror 503 is shifted in a direction indicated by a direction Move5, the stains such as the carbon contaminant C501 or the like are moved to be in the illuminated spot Spot502. Thus, when the illuminated spot Spot502 is irradiated with the cleaning light including the DUV light, stains such as carbon contaminants or the like can be decomposed and removed.

Such a multi-layer mirror for EUV that is a diffraction grating and polarizes light to near-infrared light on a long wavelength side with a wavelength different from that of EUV light is disclosed by, for example, Michael Kriese, et al, "Development of EUVL Collector Technologies for Infrared Radiation Suppression," International Symposium on Extreme Ultraviolet Lithography (2013).

Although the exemplary embodiments of the present invention have been described so far, the present invention can be modified as appropriate while still achieving the objects and having advantages of the present invention and will not be limited by the above exemplary embodiments.

For example, in the exemplary embodiments, although a laser for cleaning is provided separately from the illumination light, it is not limited to this. A light source that generates light including EUV light and DUV light and a diffraction grating that disperses the light into illumination light including EUV light and cleaning light including DUV light may be included, and the illumination light may be incident on an illuminated spot on a reflective surface, and a part of the reflective surface may be irradiated with the cleaning light. In such a case, it is preferable to further include a condenser lens for collecting the cleaning light.

For example, when a member other than a plate-like or discoid member is used as the drop-in mirror, stains such as carbon contaminant or the like may be decomposed and removed by cleaning light.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

The invention claimed is:

1. A mask inspection apparatus comprising a drop-in mirror comprising:
   a multi-layer film; and
   a reflective surface that is the surface of the multi-layer film, wherein
      the drop-in mirror is configured to reflect an illumination light incident on the reflective surface and illuminate a mask, the illumination light including EUV light,
      an area of the reflective surface is configured to be greater than an area of an illuminated spot irradiated with the illumination light on the reflective surface,
      the drop-in mirror is configured to be movable,
      a position of the illuminated spot on the reflective surface is configured to be moved when the drop-in mirror is moved,
      a part that a carbon contaminant is deposited by the EUV light on the reflective surface, which has been moved outside the illuminated spot, is configured to be irradiated with a cleaning light with a wavelength different from a wavelength of the illumination light, and
   the drop-in mirror is configured to reflect the illumination light at the same time as the cleaning light.

2. The mask inspection apparatus according to claim 1, further comprising:
   a light source configured to generate light comprising EUV light and DUV light; and
   a diffraction grating configured to disperse the light into the illumination light comprising the EUV light and the cleaning light comprising the DUV light.

3. The mask inspection apparatus according to claim 1, wherein the drop-in mirror is configured to be disposed in an apparatus exhausted by a vacuum pump.

4. The mask inspection apparatus according to claim 1, further comprising a condenser lens configured to collect the cleaning light on the part.

* * * * *